United States Patent [19]

Liu et al.

[11] Patent Number: 4,622,105
[45] Date of Patent: Nov. 11, 1986

[54] METHOD FOR MEASURING GASEOUS SULFUR DIOXIDE

[75] Inventors: Qing-Guo Liu, Philadelphia; Wayne L. Worrell, Narberth, both of Pa.

[73] Assignee: University Patents, Inc., Norwalk, Conn.

[21] Appl. No.: 605,708

[22] Filed: Apr. 30, 1984

Related U.S. Application Data

[63] Continuation of Ser. No. 303,320, Sep. 17, 1981, abandoned.

[51] Int. Cl.⁴ ............................................. G01N 27/46
[52] U.S. Cl. ................................... 204/1 T; 204/424
[58] Field of Search ............... 204/1 S, 1 F, 421–429; 429/33, 104, 191

[56] References Cited

U.S. PATENT DOCUMENTS

| | | | |
|---|---|---|---|
| 2,852,591 | 9/1958 | Ruben | 429/153 |
| 3,201,736 | 8/1965 | Ovshinsky | 338/25 |
| 3,506,492 | 4/1970 | Buzzelli et al. | 429/191 |
| 3,622,488 | 11/1971 | Chand | 204/415 |
| 3,718,546 | 2/1973 | Salzano et al. | 204/1 F |
| 3,726,718 | 4/1973 | Mellors | 429/112 |
| 3,756,923 | 9/1973 | Dahms | 204/415 |
| 4,225,656 | 9/1980 | Lunden et al. | 429/191 |
| 4,282,078 | 8/1981 | Chamberland et al. | 204/426 |
| 4,295,939 | 10/1981 | Poirer et al. | 204/1 S |

FOREIGN PATENT DOCUMENTS

| | | | |
|---|---|---|---|
| 1002599 | 12/1976 | Canada | 324/23 |

OTHER PUBLICATIONS

Gauthier et al., "J. Electrochem. Soc.", 124, No. 10 (Oct. 1977), pp. 1579–1583.
Gauthier et al., "J. Electrochem. Soc.", 124, No. 10 (Oct. 1977), pp. 1584–1587.
Jacob et al., "J. Electrochem. Soc.", 126, No. 11, (Nov. 1979), pp. 1842–1847.
Gauthier et al., "J. Electrochem. Soc.", 128, No. 2, (Feb. 1981), pp. 371–378.

*Primary Examiner*—T. Tung
*Attorney, Agent, or Firm*—Woodcock Washburn Kurtz Mackiewicz & Norris

[57] ABSTRACT

An improved gaseous sulfur dioxide galvanic cell is formed by utilizing a solid electrolyte composed of a mixture of lithium sulfate and silver sulfate. A reference electrode is formed by placing a solid mixture of the electrolyte mixture and metallic silver in contact with a portion of the surface of the solid electrolyte. A gas-type detector electrode is provided by contacting the solid electrolyte with a gold lead at a point spatially separated from the contact point between the reference electrode and electrolyte. Catalyst means are preferably provided to convert the sulfur dioxide to an equilibrium mixture of sulfur dioxide and sulfur trioxide near the electrolyte detector electrode surface. The electrolyte is preferably heated to a temperature at which it is a two-phased mixture of solid solutions for increased long term stability.

6 Claims, 4 Drawing Figures

METHOD FOR MEASURING GASEOUS SULFUR DIOXIDE

This is a continuation of application Ser. No. 303,320, filed 9/17/81 now abandoned.

BACKGROUND OF THE INVENTION

1. Field of the Invention

The invention relates to improved solid state galvanic-cell sensors for measuring the concentration of gaseous inorganic acid anhydrides, especially sulfur dioxide.

Sulfur and sulfur dioxide ($SO_2$) are important chemical species in many high temperature systems. The detection and measurement of the presence and concentration of sulfur dioxide and other inorganic sulfur-containing gaseous compounds which may, for example, be generated and released as effluents in the operation of these high-temperature systems has, in recent years, generated considerable interest with the growing concern regarding atmospheric pollution. Concentrations of sulfur dioxide as low as about 1 part per million (ppm) are believed by some to be injurious to plant life while concentrations of 400 to 500 ppm may be fatal to humans. Additionally, in the presence of moisture, $SO_2$ gas reacts to sulfurous and eventually sulfuric acid causing considerable corrosion problems and the phenomenon known as "acid rain". Over the years, various techniques, including electrochemical techniques have been developed for detecting the presence of $SO_2$.

Among the earliest of the electrochemical techniques was the bubbling of air believed to be contaminated with sulfur dioxide through deionized water and detecting the presence of the gas through changes in the water's conductivity. The use of different electrolytes and electrode materials has provided improved response time and accuracy. For example, U.S. Pat. No. 3,622,488 to Chand et al discloses the use of a liquid acidic electrolyte such as sulfuric acid with an inert (noble) metal sensing electrode and a solid, counter electrode. The counter electrode comprises an electroactive material capable of being reduced when interconnected with the sensing electrode and placed in contact with the electrolyte. The presence and concentration of sulfur dioxide at the sensing electrode is indicated by the magnitude of current between the sensing and counter electrodes.

H. Dahms in U.S. Pat. No. 3,756,923 describes a system utilizing a thin layer of liquid electrolyte containing silver ions held to the surface of a sensor electrode together with a counter electrode immersed in the liquid. The sample gas is exposed to the liquid electrolyte and the concentration of $SO_2$ determined by the change in current between the electrodes.

Salzano et al in U.S. Pat. No. 3,718,546 describe a potentiometric determination of sulfur dioxide using an electrochemical cell having a molten, fused salt electrolyte composed of a combination of lithium sulfate ($Li_2SO_4$), potassium sulfate ($K_2SO_4$) and sodium sulfate ($Na_2SO_4$). A reference gas electrode containing a known concentration of sulfur dioxide in air and a sample gas electrode containing an unknown concentration of sulfur dioxide in air are placed in contact with the electrolyte. The difference of electromotive potential between the two electrodes can be related to the concentration of sulfur dioxide in the sample gas.

A solid electrolyte and solid reference electrode may be combined to yield a compact, simple solid state galvanic-cell detector. M. Gauthier et al describe in "Solid-State Detectors for the Potentiometric Determination of Gaseous Oxides", *Journal of the Electrochemical Society: SOLID-STATE SCIENCE AND TECHNOLOGY*, October 1977 (pp. 1579–1583) two galvanic cells employing potassium and silver sulfates for the measurement of $SO_2$ concentrations in air. In a subsequent article entitled "Progress in the Development of Solid-State Sulfate Detectors for sulfate Oxide", *Journal of the Electrochemical Society: SOLID-STATE SCIENCE AND TECHNOLOGY*, February 1981 (pp. 371–378), Gauthier et al disclose yet a third potassium sulfate-silver sulfate solid state galvanic-cell for the detection and measurement of sulfur dioxide, but reveal that the potential measurements of each of these three described Gauthier potassium sulfate based solid state cells drift when used over a period of weeks or even days. These cells are also believed to be the subject of Canadian Pat. No. 1,002,599.

It would be highly desirable to provide a simple, solid state detector for $SO_2$ and similar inorganic acid anhydrides which detector would have greater potentiometric stability than heretofor achieved. While the more recent Gauthier et al article (1981) describes several other solid state sulfur dioxide detectors, each is mechanically more complicated and difficult to manufacture than the potassium sulfate-silver sulfate cells referred to above.

All of the potassium sulfate galvanic cell sulfur dioxide detectors described by Gauthier et al also operate at temperatures between about 700° and 900° C., apparently to provide sufficient ionic conductivity for acceptable detector response times. It is also highly desirable to provide a solid state detector which provides adequate response time while operating at lower temperatures whereby less expensive and less heat resistent materials may be employed in the construction of the detector and less heating needs to be provided in the measurement of sulfur dioxide in the atmosphere.

Jacob and Rao in an article entitled "A Solid-State Probe for $SO_2/SO_3$ Based on $Na_2SO_4$-I Electrolyte", *Journal of the Electrochemical Society: ELECTROCHEMICAL SCIENCE AND TECHNOLOGY*, pp. 1842–1847 (Vol. 126, No. 11, Nov. 1979) describe the possibility of a sulfur dioxide detecting cell employing sodium sulfate and silver sulfate. It is believed however, that such cell would suffer the drawbacks of the Gauthier et al potassium sulfate-silver sulfate cells in that it would be necessary to operate the sodium sulfate cell at a temperature above about 700° C. and the potentiometric stability of the cell would not be adequate for accurate long term gas surveillance.

OBJECTS OF THE INVENTION

It is an object of this invention to provide detectors and detecting systems which are suitable for the detection of gaseous inorganic acid anhydrides. More particularly, it is an object of this invention to provide detectors for sulfur dioxide having improved stability over time. Another object is to provide such detectors which are compact and which may be fabricated easily. Yet another object is to provide compact systems for $SO_2$ detection which may be operated at lower temperatures than previously possible. Yet another object is to provide compact galvanic cells for $SO_2$ detection which produce higher voltage response than previously possible. Yet another object is to provide such detectors having voltage outputs very close to predicted theoretical values for the detector. These and other objects will be apparent from a review of the following description.

SUMMARY OF THE INVENTION

This invention provides apparatus for detecting the activity of gaseous inorganic acid anhydrides in oxygen-containing gas streams. More particularly, this invention provides detection apparatus which are useful for the detection of sulfur dioxide, sulfur trioxide and mixtures of the two. According to one aspect of the invention such detection apparatus comprises a galvanic cell having a solid electrolyte element formed from a pair of metallic salts, at least one of the salts providing an oxy-anion of the inorganic acid anhydride to be detected. The two salts are provided in proportions such that a two-phased, solid electrolyte mixture forms therefrom at operating temperatures of the cell. Reference and detector electrodes are provided in contact with the solid electrolytic element, the detector electrode being spatially separated from the reference electrode. The system is adapted to provide a difference in electrical potential between the electrodes upon exposure of the detector electrode to the gas.

According to a second aspect of the invention, a galvanic cell is provided having a solid electrolyte formed from a mixture of lithium sulfate and silver sulfate, a first reference electrode and a second gas-type electrode, each electrode being in electrical contact with the electrolyte and spatially separated from one another. Means are also provided to convert the gaseous sulfur anhydride into sulfur dioxide or sulfur trioxide to produce a potential between the electrodes.

In a preferred embodiment of both aspects of the invention, a sulfur dioxide detector is provided having an integral sensor element comprising a solid electrolytic portion and a solid reference electrode portion. The electrolytic portion is formed from a mixture of lithium sulfate and silver sulfate while the reference electrode portion is formed from a mixture of metallic silver, silver sulfate and lithium sulfate. A gas-type detector electrode is provided at a surface of the electrolytic portion of the integral sensor element spatially separated from the solid reference electrode portion of the element. Catalyst means are further provided for converting an incoming gas stream containing oxygen and sulfur dioxide into an equilibrium mixture of sulfur dioxide, sulfur trioxide and oxygen at the detector electrode.

DETAILED DESCRIPTION OF THE INVENTION

It is believed that one source of long-term potentiometric instability of the previously referred to sodium and potassium sulfate-silver sulfate solid-state detectors is the result of reaction of the silver with sulfur anhydrides in the air. Another plausible source to the potentiometric instability is the formation of pyrosulfates due to reaction between the sulfate electrolyte and $SO_3$ in the gas mixture. Either of these two sources could create a concentration differential in the electrolyte and extraneous potentials in the cell which would change over time and thus change the potentiometric response of the sensor. It has been found that the creation of a concentration differential in the solid electrolyte can be minimized or eliminated by forming the electrolyte from a pair of metallic salts which are in a solid, two-phase state at the operating temperature of the cell such that reaction of the metal or other components of the reference electrode will not cause a change in the potentiometric response of the galvanic cell. Solid state detectors similar in construction and function to those described for the detection of $SO_2$ may be used for the detection of a variety of gaseous anyhydride compounds; the principle of our invention may be extended to those types of detectors as well.

The novel apparatus for detecting the presence of $SO_2$ comprises a reference electrode, a solid electrolytic element in electrical contact with the reference electrode and a detector electrode in electrical contact with the electrolytic element and spatially separated from the reference electrode. The active components of the electrolytic element are a pair of metallic salts, at least one of the salts providing the electrolytic element with oxy-anions of the particular anhydride being detected. The pair of metallic salts are provided at relative proportions to form a two-phase, solid mixture at the cell's operating temperatures. The reference electrode provides a fixed electrical potential. The detector electrode provides an electrical potential when the anhydride to be detected is in contact with the detector electrode and the electrolytic element. This potential changes with changes in the concentration of the anhydride. A potentiometric detector connected between the electrodes permits the measurement of the concentration of the anhydride to be detected by measuring the difference in potential between the electrodes. It may be necessary or desirable to further provide catalyst means to convert the gaseous anhydride desired to be detected into another gaseous compound of the anhydride which will react with the detector electrode to provide a potential across the reference and detector electrodes.

According to one important aspect of the invention, sulfuric anhydrides such as $SO_2$ may be detected using a solid electrolytic element formed from lithium sulfate. The second component of the electrolytic element is preferably silver sulfate which allows the use of a silver-silver sulfate-lithium sulfate solid reference electrode. Several two-phase solid mixtures of the lithium sulfate and silver sulfate exist at temperatures below 700° C. A two-phase system consisting of solid solutions of $\alpha$-$Li_2SO_4$ and $(Ag,Li)_2SO_4$, which exists between about 510° and 560° C. for proportions of lithium sulfate between about 80 to 64 mole percent with proportions of silver sulfate between about 20 and 36 mole percent, is preferred.

According to yet another important feature of the invention a solid reference electrode is formed for use with a solid electrolyte by mixing the electrolyte mixture with a metal of one of the metallic salts forming the electrolyte. Embedding silver in the described lithium sulfate-silver sulfate electrolyte mixtures minimizes or virtually eliminates sulfation of the silver by the gaseous atmosphere.

According to yet another important feature of the invention, the electrolytic element and reference electrode may preferably be formed as a single integrated element so as to provide good electrical contact and to assure that the electrical potential at the electrode-electrolyte interface is established solely by the reference electrode. A layer of the mixed silver sulfate and lithium sulfate components of the electrolytic element and a layer of mixed silver, lithium sulfate and silver sulfate components of the solid reference electrode may be compressed together in a single operation. The compressed, integrated element is subsequently sintered in an atmosphere containing sulfur dioxide. It is envisioned that the solid sensor elements may similarly be formed from other components for the detection of sulfuric and other anhydrides in which the electrolytic portion of the integrated solid sensor is two-phased at its operating temperature and is substantially uneffected by reactions occurring within the reference electrode.

Catalyst means for transforming the inorganic acid anhydride into a second acid anhydride, such as the transformation of $SO_2$ into $SO_3$, is generally useful in the practice of the described embodiments of the invention. The detector electrodes of the lithium sulfate-silver sulfate cells of this invention are believed to respond to the activity of sulfur trioxide. Therefore, catalyst means are preferably provided for converting the sample gas stream containing $SO_2$ and $O_2$ into an equilibrium mixture of $O_2$, $SO_2$, and $SO_3$ near the detector electrode. Where the preferred, two-phased embodiment of the lithium and silver sulfates and other single phased embodiments of that cell are operated at temperatures less than about 600° C., vandium pentoxide may be successfully employed to create the equilibrium mixture of $SO_2$, $SO_3$ and $O_2$. Other catalysts will be understood by those skilled in the art to be similarly useful. p Solid mixtures of metals and metallic compounds, especially oxides or sulfates $M_xO-M_xSO_4$ (M representing metal), may be used as solid reference electrodes for solid galvanic cells. However, the silver-silver sulfate ($Ag-Ag_2SO_4$) combination is preferable because it not only gives fixed sulfur trioxide potentials, but also good electric contact at th electrolyte/reference electrode interface. Silver is a unique metal that is stable in oxidizing atmospheres at temperatures over about 200° C.; its sulfate ($Ag_2SO_4$), is also stable.

A comparison of different binary systems of $Ag_2SO_4$ with alkali and alkali earth metal sulfates indicates that the $Li_2SO_4$ and $Ag_2SO_4$ binary system is preferred for detection of $SO_2$ in gaseous streams. A phase diagram of this binary system is provided at page 315 of *PHASE DIAGRAMS FOR CERAMISTS, 1975 SUPPLEMENT*, E. M. Levin et al, The American Ceramic Society, Inc. (1975), which is incorporated herein by reference. The $Li_2SO_4$ has an FCC structure at high temperature and $Ag_2SO_4$ a rhombic structure. There are two high conductivity phases in this system, $\alpha-Li_2SO_4$ and $(Ag,Li)_2SO_4$, both solid solutions. These two high conductivity phases co-exist with good conductivity between about 510° C. and 560° C. The activity of $Ag_2SO_4$ remains constant in this two phase region, no matter how the composition of the binary system changes. In comparison, $Na_2SO_4-Ag_2SO_4$ and $K_2SO_4-Ag_2SO_4$ systems each forms a continuous solid solution (single phase) over its entire range of compositions at high temperatures. Thus galvanic cells formed using these solid solutions as electrolytes are more susceptible to variations in the concentration of the silver sulfate. Variations in concentrations may be caused either by reaction of the silver in the reference electrode with $SO_3$ to form $Ag_2SO_4$ or by decomposition of the $Ag_2SO_4$.

Another advantage of the $Li_2SO_4$ system over the $Na_2SO_4$ and $K_2SO_4$ systems is the higher conductivity due to the smaller ionic radius and higher mobility of the lithium ions, which provides adequate sensor response times a lower temperatures. Also the two phase electrolytes have less absorption of water vapor and improved mechanical properties. The operation of our lithium sulfate-silver sulfate cells with silver-lithium sulfate-silver sulfate solid reference electrode is believed to be as follows.

In $Li_2SO_4-Ag_2SO_4$ electrolytes, the lithium ions are the predominant mobile species. The electromotive force ("emf") across the electrolyte is given by the equation

$$E = \frac{1}{F} \int_{\mu_{Li}'}^{\mu_{Li}''} t_{ion} \, d\mu_{Li} \quad (2)$$

where E is the emf and $\mu_{Li}''$, $\mu_{Li}'$ are the chemical potentials of lithium on each side of the electrolyte. Rewriting the chemical potentials in terms of activities, and with $t_{ion}=1$ (ionic transference number), $$E = \frac{RT}{F} \ln \frac{a_{Li}''}{a_{Li}'} \quad (3)$$

It is believed that the activities of lithium are fixed by the composition of the gas according to the following reaction at detector electrode $$Li_2SO_4 = 2Li + SO_3 + \tfrac{1}{2}O_2$$

and at reference electrode

$$2Ag + Li_2SO_4 = Ag_2SO_4 + 2Li$$

for two phase electrolyte, $a_{Li_2SO_4}$ and $a_{Ag_2SO_4}$ are constant so

At high temperatures and in the presence of a catalyst, $SO_2$, $SO_3$ and $O_2$ are in equilibrium. The partial pressure of $SO_2(p_{SO_2})$ can be substituted for the partial pressure of $SO_3$ ($p_{SO_3}$), yielding The partial pressure of $O_2$ of air is known and the unknown partial pressure of $SO_2$ or $SO_3$ can be calculated from the measured emf. The emf response generated for various $SO_2$ concentrations by a preferred, two-phase electrolyte embodiment of this invention and by a single-phase electrolyte embodiment, are depicted graphically in FIG. 3. As can be seen, the cells exhibit a proportionate and substantially linear variation for a logarithmic variation of the concentration of the $SO_2$, $SO_3$ equilibrium mixtures.

Figure 1:
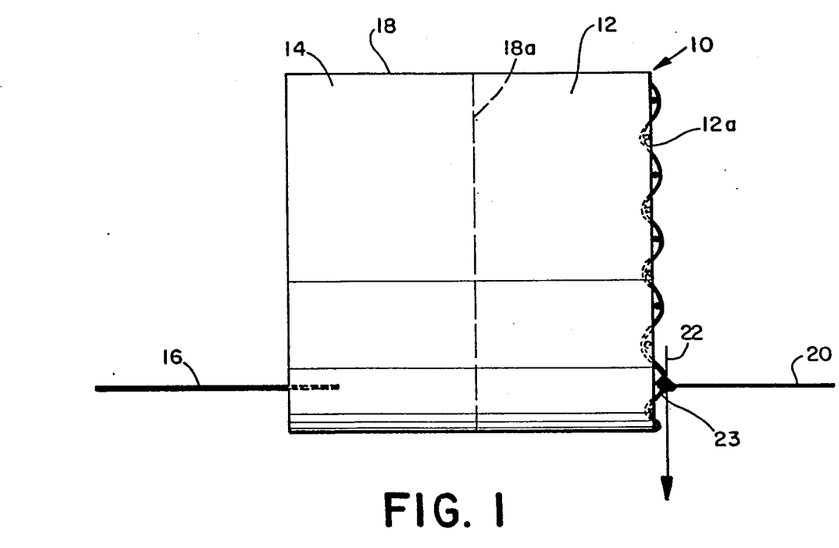
FIG. 1 is a diagrammatic view of a solid state galvanic cell of the present invention.

An exemplary embodiment of a solid state galvanic cell 10 according to the present invention is depicted diagrammatically in FIG. 1. The cell 10 comprises a solid electrolyte 12 formed from a mixture of lithium sulfate and silver sulfate and a solid reference electrode 14 formed from a mixture of silver and the mixture of the electrolyte components (i.e. silver sulfate and lithium sulfate in the same proportions as the electrolyte) and having a lead 16 for electrical contact extending therefrom. Although the electrolyte 12 and reference electrode 14 may be formed separately and placed in contact with one another, preferably they are formed as a single integral sensor element 18 to provide good electrical contact between them and to prevent the intrusion of air or other contaminant into their interface, which is indicated diagrammatically by the dashed line 18a. The lead 16 is of a nonreactive material such as gold. The use of silver in the lead 16 is to be avoided as its reaction with $SO_2$, $SO_3$ or both in the sample gas may lead to failure of the lead 16. A gas type detector electrode is formed by providing a second, nonreactive lead 20 in electrical contact with the electrolyte 12 at a surface 12a of the electrolyte 12 which is spatially separated from the reference electrode 14 and passing the sample gas, represented by the arrow 22, over the lead 20 and electrolyte surface 12a. A platinum mesh 23 has been embedded in the electrolyte 12 and is partially exposed at a surface 12a of the electrolyte spatially separated from the solid reference electrode 14. In the depicted embodiment, the platinum mesh 23 is welded to the lead 20 to provide a large electrode-electrolyte surface area with which the active anhydride of the sample gas may react. The platinum mesh also assists in maintaining an equilibrium mixture of oxygen, sulfur dioxide and sulfur trioxide at the detector electrode surface 12a of the cell 10. It is believed that the reaction at that electrode involves preferably sulfur trioxide rather than sulfur dioxide. Tests made without a catalyst produced emf values lower than predicted for the $SO_2$ concentrations involved.

Powdered, anhydrous 99.999% pure $Li_2SO_4$ and $Ag_2SO_4$ were used to make the electrolytes. Solid reference electrodes were made by mixing ⅔ (by weight) of powdered 99.99% pure silver and ⅓ (by weight) of the $Li_2SO_4$-$Ag_2SO_4$ electrolyte powder. Each component was first passed through a U.S. Standard Sieve 325 mesh. The electrolyte components were throughly mixed and then compressed with a pressure of about 20,000 psi. The resulting aggregate was reduced to a size which allowed it to pass through a U.S. Standard Sieve No. 50 mesh. The solid reference electrode components were similarly passed through a U.S. Standard Sieve No. 325 mesh, throughly mixed, compressed at a pressure of about 20,000 psi and broken up sufficiently to pass through a U.S. Standard Sieve No. 50 mesh. The galvanic cells 10 were additionally provided with a platinum wire mesh at the gas electrode surface 12a of the electrolyte 12. The gold lead 20 of the gas electrode was welded to an exposed portion of the mesh 23. The platinum mesh 23 and welded gold wire 20 were placed in the bottom of a rubber mold. The −50 mesh electrolyte powder mix was added to the mold and tamped by hand. The −50 mesh reference electrode mix was added to the mold and a gold wire lead inserted therein. The mold was placed in a hydraulic isostatic press and subjected to a pressure of approximately 80,000 pounds per sq. in. The cell 10 was removed from the mold and the gas electrode surface 12a cleaned to expose the platinum mesh 23. The cell 10 was thereafter sintered for approximately 50 hours in an atmosphere of about 100 parts per million sulfur dioxide in air. The preferred electrolytes in the two-phase $\alpha$-$Li_2SO_4$ and $(Ag,Li)_2SO_4$ solid solutions range were fabricated by using a mixture of approximately 23 mole percent $Ag_2SO_4$ and 77 mole percent $Li_2SO_4$. Single-phase electrolytes, one about 5 mole percent $Ag_2SO_4$ and 95 mole percent $Li_2SO_4$ in the $\alpha$-$Li_2SO_4$ solid solution region and the other about 55 mole percent $Ag_2SO_4$ and 45 mole percent $Li_2SO_4$ in $(Ag, Li)_2SO_4$ solid solution region, were also prepared for comparison. Sintering temperatures were about 730° C. for 95 mole percent $Li_2SO_4$-5 mole percent $Ag_2SO_4$ electrolytes and about 530° to 540° C. for the preferred 77 mole percent $Li_2SO_4$-23 mole percent $Ag_2SO_4$ and the remaining 45 mole percent $Li_2SO_4$-55 mole percent $Ag_2SO_4$ electrolytes. The former cell was operated at a temperature of about 700° C. While the latter two cells, including the preferred type, were operated at a temperature of about 530° C.

Figure 2:
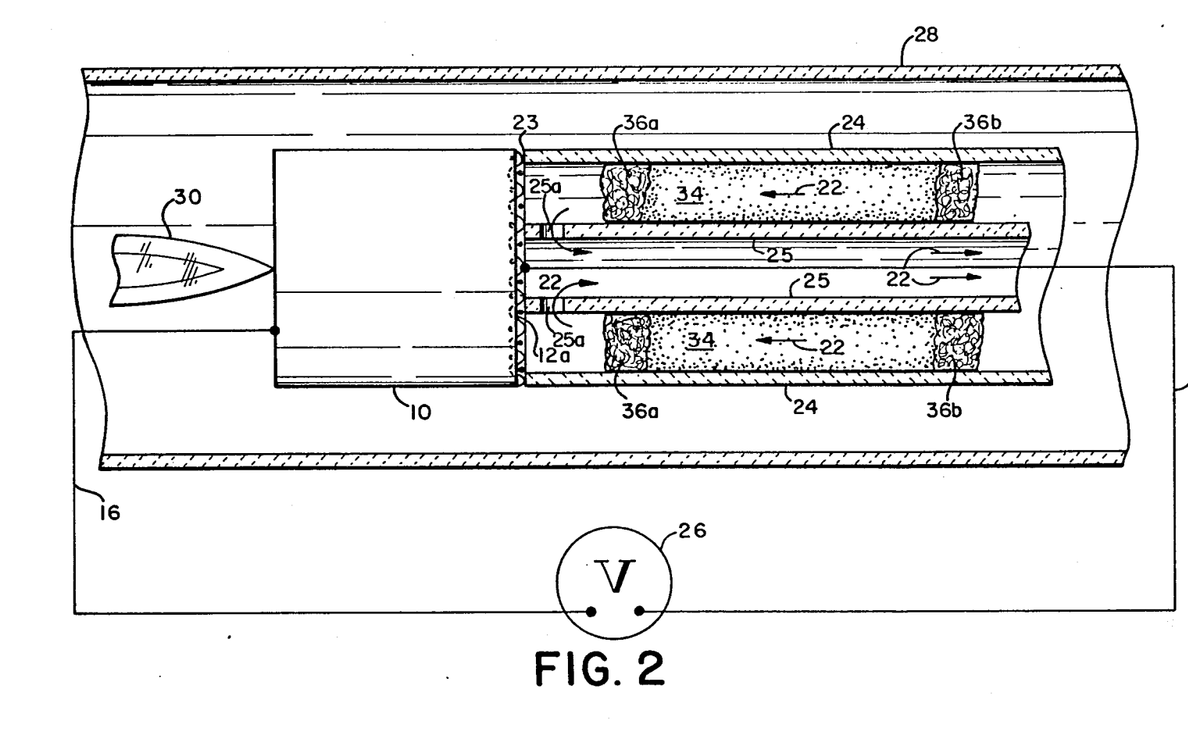
FIG. 2 is a diagrammatic partially sectioned view of a test detection apparatus incorporating the solid state galvanic cell of FIG. 1 for the measurement of $SO_2$.

An apparatus for detecting $SO_2$ using the integral solid cells 10 of FIG. 1, was fabricated as is depicted in FIG. 2. Sample gas, again indicated by arrows 22, was circulated to the detector electrode surface 12a of the cell 10, where platinum mesh 23 was again exposed, by means of a pair of concentric silica ($SiO_2$) tubes 24 and 25 which where centered on the surface 12a. Silica was preferred for its inertness, thermal shock capability and price, but other materials and other means to channel sample gas to and from the detector electrode surface 12a of the cell may be used. The tubes 24 and 25 were held against the surface 12a of the cell by an arrangement of tension springs and wires (not depicted) which resulted in an essentially gas type seal between the surface 12a and the end of the tubes 24 and 25. Again, a gold detector electrode lead 20 was welded to the mesh 23 and run along the innermost tube 25 and through an opening (not depicted). A second, gold electrode 16 was again embedded in the solid reference electrode portion of the cell 10. The apparatus was placed in an electric furnace, depicted illustratively by its furnace tube 28. The leads 16 and 20 were connected electrically with a potentiometric measuring device 26 located outside the furnace 28. The temperature of the integral cell 10 was monitored by a thermocouple 30. A sample gas 22 was conducted to the detection electrode face 12a of the cell 10 in the gap formed between the concentric silica tubes 24 and 25 passed through openings 25a at the base of the innermost tube 25 and along the length of the tube 25 away from the cell 10 to a venting apparatus (not depicted). The vanadium pentoxide powder 34 is provided in the gap between the two tubes 24 and 25. Quartz wool 36a and 36b was packed around the gap at either end of the powder 34 to keep the powder in position and prevent it from contacting the cell 10. The vanadium pentoxide powder 34 was the primary catalyst used to obtain equilibrium mixtures of $SO_2$, $SO_3$ and $O_2$ in the preferred and other cell 10 embodiment operated below 600° C. (specifically, at 530° C.). In the one exemplary embodiment cell 10 operated at about 700° C. (5 mole percent silver sulfate-95 mole percent lithium sulfate) a large mass of platinum wire (not depicted) was substituted for the vanadium pentoxide catalyst 34 in the gap between the concentric tubes 24 and 25 upstream from the detector electrode surface 12a.

The test furnance 28 provided an essentially constant (±1° C.) temperature zone within which the cell 10 was positioned. Test gases were supplied with $SO_2$ concentrations of 20, 100, 204, 500, 1000 ppm and 10,000 ppm (1%) by volume and were mixed with air in a mixing chamber (not depicted) before being passed into the tube 24 to vary the composition of tested gases. The emf was measured by a high impedance potentiometric electrometer coupled with a chart recorder.

The presence of a catalyst was necessary to obtain equilibrium between $SO_2$, $SO_3$ and $O_2$ for the detection of $SO_2$ in the tested gases. When a gold mesh was substituted for platinum mesh 23 of FIG. 1 the values of the emf were less than theoretical values when the vanadium oxide catalyst was also removed. It can be concluded therefore that the electrochemical reaction involves preferably $SO_3$ rather than $SO_2$ and that conversion of $SO_2$ into $SO_3$ is required for preferred use of the sensor. Two kinds of catalysts were successfully employed as described, a 0.2 mm diameter platinum wire and vanadium pentoxide powder.

The emf of the cell 10 is stable and reproducible, especially for the preferred, two-phase lithium sulfate-silver sulfate electrolyte sensors. In order to check the reversibility of their emf, a small external current (6 microamps) was passed through a two-phase electrolyte cell in both directions for 30 seconds. The emf was restored to the original values (within ±0.5 mV) in 2 minutes.

Figure 3:
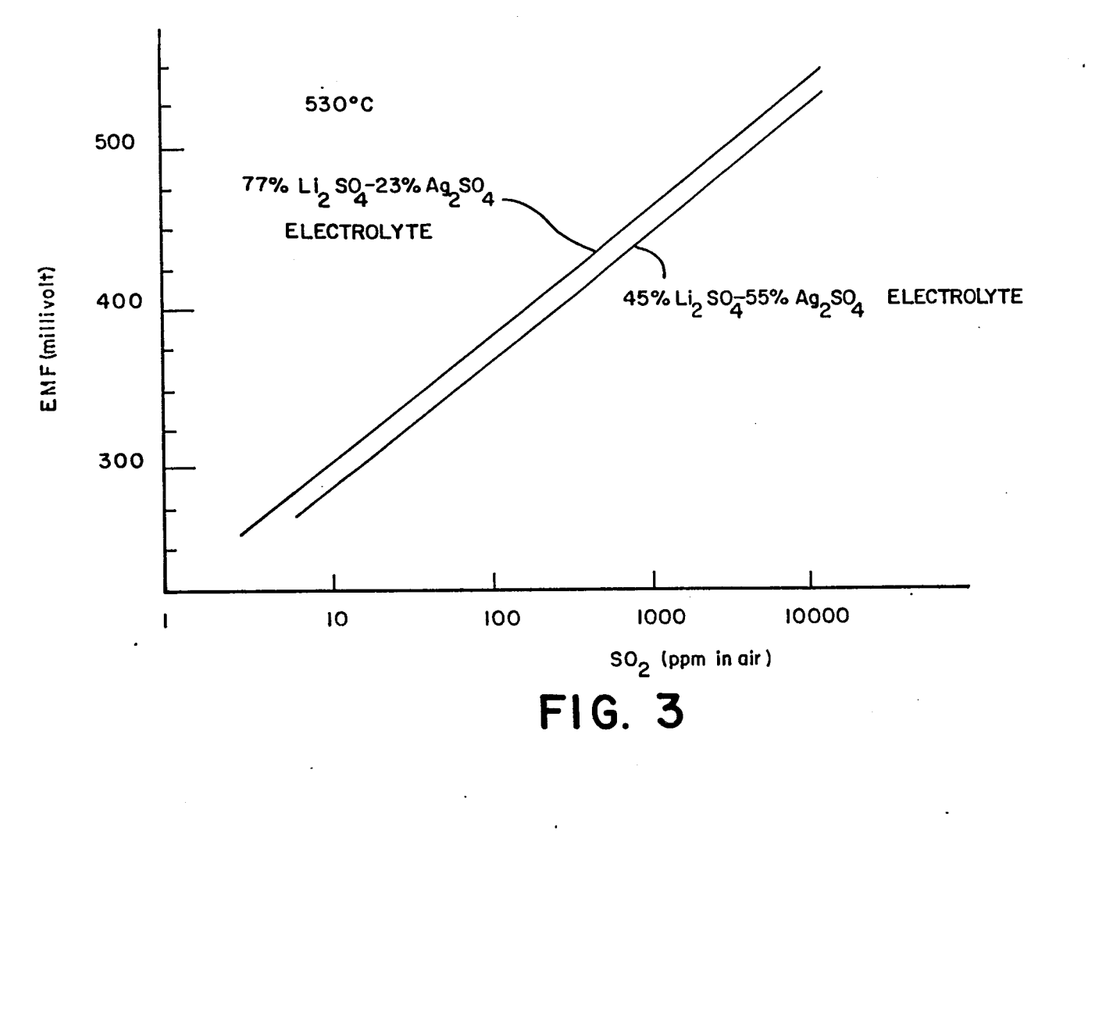
FIG. 3 depicts graphically the measured potentiometric response of two embodiments of the galvanic cell sensors of FIGS. 1 and 2 for indicated concentrations of sulfur dioxide in equilibrium with sulfur trioxide and oxygen.

The results of the emf dependence of two embodiments of the galvanic cells 10 on $SO_2$ compositions of inlet gases are depicted graphically in FIG. 3. The horizontal axis of the figure represents the inlet gas $SO_2$, ppm concentrations (by volume) in air, which is proportional to the partial pressures of $SO_3$ if equilibrium among $SO_2$, $SO_3$ and $O_2$ is achieved. The solid lines are the measured emf responses for the preferred embodiment cell (77 mole percent lithium sulfate-23 mole percent silver sulfate electrolyte with a solid reference electrode formed from $\frac{2}{3}$ by weight powdered silver with $\frac{1}{3}$ by weight electrolyte) and a second, single phase cell embodiment (45 mole percent lithium sulfate-55 mole percent silver sulfate solid electrolyte with a solid reference electrode) formed from $\frac{2}{3}$ by weight silver and $\frac{1}{3}$ by weight electrolyte mixture. Both cells were fabricated in the manner previously described and operated using a device comparable to that depicted in FIG. 2 at 530° C. The preferred, two-phase embodiment was used to measure concentrations from a few ppm to more than 10,000 ppm $SO_2$ in equilibrium with $O_2$ and $SO_3$. It is believed that an even greater range of measurement can be achieved using the preferred, two-phase system. The measured emf responses of the cells appear to be within about 5 millivolts of the theoretical values across the range of concentrations depicted.

Intereference in the $SO_2$-$SO_3$ response of the preferred two-phase electrolyte sensors was tested by using the aforesaid two-phase (77 mole % lithium sulfate-23 mole % silver sulfate) electrolyte sensor at 530° C. with various concentrations of carbon dioxide gas (between about 8 and 24% by volume) added to concentrations of between 10 and 1000 part per million (by volume) of $SO_2$ in air. Variations between the measured emf response of the galvanic cell 10 and the theoretical values for the cell were less than 3 millivolts. The preferred two-phase electrolyte cell 10 was also tested for sensitivity to water vapor. Cell 10 using the preferred, two-phase 77% lithium sulfate-23% silver sulfate electrolyte was again tested at 530° C. with concentrations of about 110 part per million $SO_2$ (by volume) and between about 0.5% and 7.3% (by volume) $H_2O$ in air. The maximum variation of the cell 10 produced emf from predicted theoretical emf values with added water was about one millivolt. It is suggested, however, for longevity of the sensor that water vapor content of the sample gas be reduced to the lowest possible levels as pitting was noticed on the detector electrode surface 12a of the cell 10.

Figure 4:
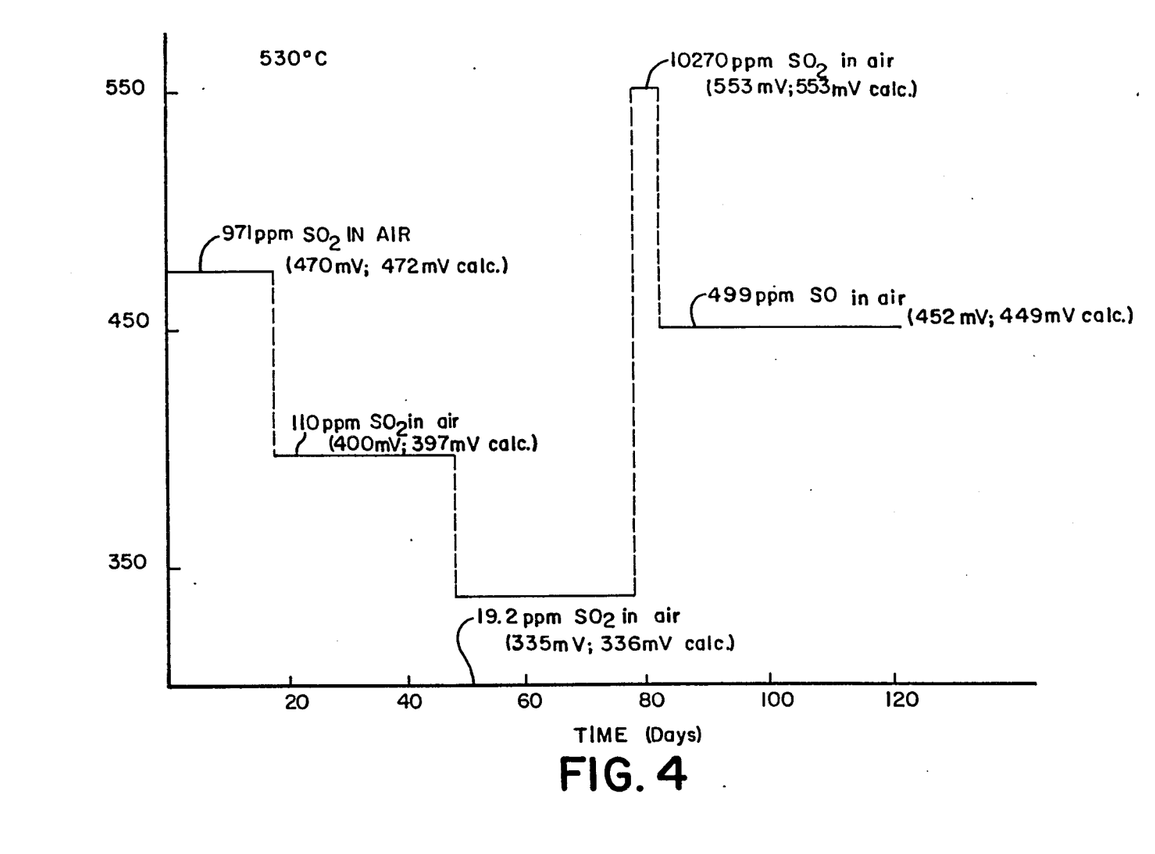
FIG. 4 depicts graphically the least square values of the measured potentiometric response of a preferred, two-phase lithium sulfate-silver sulfate electrolyte galvanic cell for indicated $SO_2$ equilibrium concentrations in air tested on a daily basis by the same galvanic cell.

FIG. 4 depicts the results of a long term stability test to which a preferred, two-phase electrolyte (77% lithium sulfate-23% silver sulfate) cell 10 having a solid reference electrode of the same two-phase electrolyte mixture (one-third by weight) and silver (two-thirds by weight) is currently being subjected. Solid lines indicate the emf response of the two-phase system for identified concentrations of $SO_2$ (by volume) in air plotted for the days when each such indicated concentration was measured by the sensor. The emf responses and the calculated, theoretical emf values for the cell 10 are indicated in parentheses. The sensor has been operated continuously for 121 consecutive days to date. The vertical lines denote when changes have been made in the $SO_2$ concentrations. The emf responses of the sensor have been within about 5 millivolts of the calculated, theoretical response of the cell for the gas concentrations employed. The emf stability achieved to date by this two-phase galvanic cell detector is far superior to that reported by Gauthier et al in the afore-referenced article "Progress in Development of Solid-State Sulfate Detectors for Sulfur Dioxide" (1981) for three $SO_2$ detectors using a potassium sulfate electrolyte with silver and/or silver sulfate solid reference electrodes. The results are also superior to those reported in the same article for other, more complicated $SO_2$ detectors employing magnesium sulfate-magnesium oxide ($MgSO_4$-$MgO$) or maganese sulfate-manganese oxide ($MnSO_4$-$MnO$) solid reference electrodes or potassium sulfate-zirconia based electrolytes. Based upon the encouraging results to date it is envisioned that the preferred two-phased lithium sulfate-silver sulfate detector ($\alpha$-$Li_2SO_4$ and $(Ag,Li)_2SO_4$ solid solutions) will produce emf responses within a few millivolts of predicted theoretical values for at least 6 months or more.

It is further envisioned that the described sulfur dioxide detectors may be used with an oxygen detector in the manner described in yet another Gauthier et al article entitled "Solid-State Dectectors for the Potentiometric Determination of Gaseous Oxides", *Journal of the Electrochemical Society: SOLID-STATE SCIENCE AND TECHNOLOGY*, October 1977 (pp. 1584–1587), for the measurement of $SO_2$, $SO_3$ or other gaseous anhydrides in oxygen variable gases.

It will be appreciated by one skilled in the art that although the described, single-phase lithium sulfate-silver sulfate electrolyte solid state galvanic cells do not provide the long-term stability of the preferred, two-phase systems, each does, however, provide response and stability at operating temperatures significantly less than about 700° C. to rival the use of the previously referred to potassium sulfate-silver sulfate and sodium sulfate-silver sulfate galvanic cells, which require operating temperatures in excess of 700° C. for short term measurements. Moreover, it will be appreciated by one skilled in the art that although the described galvanic cells have been described as being used with a potentiometric device to measure $SO_2$ concentrations, the potential difference of the cell may be used in other ways such as through an alarm circuit or light to merely indicate the presence of $SO_2$ (or $SO_3$) or a minimum concentration of those gases.

While preferred embodiments of the invention have been described, changes to the composition, form and components of the solid state integral sensors and the detection apparatus of this invention may be made by one skilled in the art without departing from the scope of the invention which is more fully defined in the following claims.

What is claimed:

1. A method for measuring sulfur dioxide or sulfur trioxide in an oxygen-containing gas comprising:

contacting the gas with a solid electrolyte comprising lithium sulfate and silver sulfate, the electrolyte being in electrical contact with a solid reference electrode comprising lithium sulfate, silver sulfate and silver in intimate admixture; and measuring the electrical potential between the electrolyte and the reference electrode;

said electrolyte being maintained at a temperature during the contacting wherein it comprises two conductive phases.

2. The method of claim 1 further comprising treating the gas with a catalyst means for effecting substantially an equilibrium mixture of sulfur dioxide and sulfur trioxide in the gas prior to contacting said gas with the electrolyte.

3. The method in claim 1 wherein said temperature is less than about 700° C.

4. The method of claim 1 wherein said temperature is between about 515° C. and about 560° C.

5. The method of claim 1 wherein said electrolyte consists essentially of from about 64 to about 80 mole % of lithium sulfate and from about 20 to about 36 mole % of silver sulfate.

6. The method of claim 1 wherein said reference electrode comprises lithium sulfate and silver sulfate in about the same molar proportions as found in the solid electrolyte.

* * * * *